(12) United States Patent
Harimoto et al.

(10) Patent No.: US 6,436,311 B1
(45) Date of Patent: Aug. 20, 2002

(54) SAMPLING MATERIAL FOR A CARBONYL COMPOUND IN A GAS

(75) Inventors: Takashi Harimoto; Kazuya Kitasaka; Shinji Hirose, all of Osaka (JP)

(73) Assignee: Sumika Chemical Analysis Service, Ltd., Osaka (JP)

( * ) Notice: Subject to any disclaimer, the term of this patent is extended or adjusted under 35 U.S.C. 154(b) by 0 days.

(21) Appl. No.: 09/720,715

(22) PCT Filed: Jun. 30, 1999

(86) PCT No.: PCT/JP99/03543

§ 371 (c)(1),
(2), (4) Date: Dec. 28, 2000

(87) PCT Pub. No.: WO00/02041

PCT Pub. Date: Jan. 13, 2000

(30) Foreign Application Priority Data

Jul. 1, 1998 (JP) .............................................. 10-223538

(51) Int. Cl.[7] .......................... C09K 3/00; C07C 67/00; G01N 30/00; G01N 1/22; B01J 39/08
(52) U.S. Cl. ..................... 252/181.1; 252/184; 252/189; 252/182.2; 252/182.23; 252/182.34; 252/964; 510/100; 436/167; 436/128; 436/126; 436/130; 422/83; 422/88; 422/56; 422/57; 422/58; 422/59
(58) Field of Search ............................ 252/181.1, 181.7, 252/184, 189, 964, 182.23, 182.29, 182.31, 182.34; 510/100; 436/128, 130, 126, 167; 422/56, 57, 58, 59, 83, 88

(56) References Cited

U.S. PATENT DOCUMENTS 4,380,587 A * 4/1983 Koocher ..................... 436/128
4,990,458 A * 2/1991 Rosefeld ..................... 436/174

FOREIGN PATENT DOCUMENTS

| EP | 0 140 886 B1 | * | 7/1988 |
|---|---|---|---|
| JP | 545874 A | | 1/1979 |
| JP | 545874 | | 1/1979 |
| JP | 56129027 | | 10/1981 |
| JP | 56129027 A | | 10/1981 |
| JP | 60500882 | | 6/1985 |
| JP | 60500882 A | | 6/1985 |
| JP | 60161858 | | 10/1985 |
| JP | 6161464 | | 4/1986 |
| JP | 3232516 | | 10/1991 |
| JP | 4197435 | | 7/1992 |
| JP | 9157328 A | | 6/1997 |
| JP | 9157328 | | 6/1997 |
| WO | WO 84/04165 | * | 10/1984 |

* cited by examiner

Primary Examiner—Joseph D. Anthony
(74) Attorney, Agent, or Firm—Birch, Stewart, Kolasch & Birch, LLP

(57) ABSTRACT

A sampling material for a carbonyl compound in a gas comprising a reagent capable of converting a carbonyl compound to a derivative thereof supported on a cation exchanger; and a sampling cartridge for a carbonyl compound in a gas wherein a sampling material for a carbonyl compound in a gas comprising a reagent capable of converting a carbonyl compound to a derivative thereof supported on a cation exchanger is packed in a column are provided. The sampling cartridge can be used for analyzing a carbonyl compound such as formaldehyde with ease and at a high sensitivity and high accuracy, and has excellent storage stability.

5 Claims, No Drawings

SAMPLING MATERIAL FOR A CARBONYL COMPOUND IN A GAS

This application is the national phase under 35 U.S.C. § 371 of PCT International Application No. PCT/JP99/03543 which has an International filing date of Jun. 30, 1999, which designated the United States of America.

FIELD OF THE INVENTION

The present invention relates to a sampling material for a carbonyl compound used for capturing a carbonyl compound in a gas such as formaldehyde in air, and to a sampling cartridge for a carbonyl compound in a gas using the same.

TECHNICAL BACKGROUND

Recently, an influence of volatile organic compounds on environment is regarded as a problem. For example, caused by an airtight structure of houses, an influence of carbonyl compounds such as formaldehyde and the like diffused from building materials and furniture on housing environment and working environment is regarded as a social problem. For investigating countermeasures against such a problem, it is firstly necessary to measure correctly the amount of carbonyl compounds in air. Accordingly, development of a method which can measure the amount of carbonyl compounds such as formaldehyde in air in room and the like at a high sensitivity and at high accuracy is desired.

Currently, "aldehyde measuring cartridge" and the like prepared by packing a sampling material for a carbonyl compound in a column are commercially available for measuring the amount of an aldehyde such as formaldehyde and the like in air. As the sampling material for a carbonyl compound, for example, there is known one where a reagent capable of converting a carbonyl compound to a derivative thereof, such as 2,4-dinitrophenylhydrazine and the like, are supported on silica gel. The amount of carbonyl compounds in air can be detected by using such a sampling material for a carbonyl compound and "aldehyde measuring cartridge" packed with the sampling material, and by capturing carbonyl compounds in air by a reaction with a sampling material for a carbonyl compound in the cartridge, then, eluting the carbonyl compound derivative from the cartridge, and measuring the amount thereof.

However, the conventional "aldehyde measuring cartridge" does not have necessarily sufficient accuracy, and has a problem of storage stability and of reduction in accuracy and the like in storage for a long period of time. Further, when a carbonyl compound derivative captured by reacting a carbonyl compound with a reagent capable of converting a carbonyl compound to a derivative thereof is eluted, a reagent capable of converting a carbonyl compound to a derivative thereof which has not been reacted with the carbonyl compound is also eluted simultaneously. Consequently there is a problem that operations such as separation, removal and the like of the reagent capable of converting a carbonyl compound to a derivative thereof are necessary for quantitative analysis.

DISCLOSURE OF THE INVENTION

An object of the present invention is to provide a sampling material for a carbonyl compound in a gas which has a higher sensitivity than that of a conventional sampling material for a carbonyl compound, makes an analysis of high accuracy possible, is excellent in storage stability, and does not require, in analysis, operations such as separation, removal and the like of an unreacted reagent capable of converting a carbonyl compound to a derivative thereof. Particularly, the present invention provides a sampling material for a carbonyl compound which enables microanalysis of aldehyde compounds such as formaldehyde and the like in indoor or outdoor air.

The present inventor has found that a sampling material for a carbonyl compound where a reagent capable of converting a carbonyl compound to a derivative thereof is supported on a cation exchanger is suitable for the above-mentioned object, and that, by using this sampling material for a carbonyl compound, quantitative analysis of a carbonyl compound in a gas at a high sensitivity and at high accuracy becomes possible.

Namely, the present invention provides a sampling material for a carbonyl compound in a gas comprising a reagent capable of converting a carbonyl compound to a derivative thereof supported on a cation exchanger.

Also, the present invention provides a sampling cartridge for a carbonyl compound in a gas wherein a sampling material for a carbonyl compound in a gas comprising a reagent capable of converting a carbonyl compound to a derivative thereof supported on a cation exchanger is packed in a column.

The sampling material for a carbonyl compound in a gas of the present invention has excellent storage stability. Further, in use in analysis, a carbonyl compound derivative, namely, a reagent capable of converting a carbonyl compound to a derivative thereof which has been reacted with a carbonyl compound, can be eluted, with eluting little reagent capable of converting a carbonyl compound to a derivative thereof which has not been reacted with a carbonyl compound. Consequently, in analysis, the sampling material for a carbonyl compound in a gas of the present invention does not require operations such as separation, removal and the like of a reagent capable of converting a carbonyl compound to a derivative thereof. Therefore, quantitative analysis of a carbonyl compound is possible at simpler manner, a higher sensitivity and higher accuracy as compared with the conventional method.

The cation exchanger used in the present invention means a polymer substrate such as a resin, cellulose, silica gel and the like into which a cation exchanging group, namely, a group of which a counter ion is a cation, has been introduced. When the polymer substrate is a resin, namely, when a cation exchanger is a cation exchanging resin, examples of the cation exchanging group include a sulfonic group, carboxyl group and the like. Particularly, a strong acidic cation exchanging resin of a sulfonic acid type is preferable. When the polymer substrate is a resin, the resin is not particularly restricted. Although styrene-based resins such as crosslinked polystyrene, for example, a copolymer of styrene with divinylbenzene, are preferred, an acrylic acid-based, methacrylic acid-based resin and the like may also be used. When the polymer substrate is cellulose, namely, when a cation exchanging group is introduced into cellulose to provide a cation exchanger, examples of the cation exchanging group include a sulfoethyl group, phosphomethyl group, phosphate group, carboxymethyl group and the like. Particularly preferable are strong acidic exchangers into which a sulfoethyl group has been introduced. When the polymer substrate is silica gel, examples of the cation exchanging group include a benzensulfonic group, propylsulfonic acid, carboxyl group and the like. Particularly, those having benzenesulfonic group are preferable.

As the reagent capable of converting a carbonyl compound to a derivative thereof used in the present invention, for example, reagents capable of converting a carbonyl compound to a derivative thereof described in JP-B-2-54906 can be listed. Specific preferable examples of the reagent capable of converting a carbonyl compound to a derivative thereof include amino compounds such as O-substituted hydroxylamines, for example O-(2,3,4,5,6-pentafluorobenzyl)hydroxylamine and the like; aryl hydrazines, for example 4-nitrophenyl hydrazine, 2,4-dinitrophenyl hydrazine, 4-carboxyphenyl hydrazine, phenyl hydrazine, diphenyl hydrazine, 2-naphthyl hydrazine and the like; sulfonyl hydrazines, for example, 4-nitrobenzenesulfonyl hydrazine and the like; acyl hydrazines, for example, benzoyl hydrazine, 4-nitrobenzoyl hydrazine, 4-chlorobenzoyl hydrazine, 3-chlorobenzoyl hydrazine, 4-bromobenzoyl hydrazine and the like; and semicarbazides such as phenylsemicarbazide, tolylsemicarbazide, 3,5-dinitrophenylsemicarbazide, 1-naphthylsemicarbazide, 2-naphthylsemicarbazide and the like. Particularly, O-(2,3,4,5,6-pentafluorobenzyl)hydroxylamine and 2,4-dinitrophenylhydrazine are preferable.

A method for producing a sampling material for a carbonyl compound of the present invention is not particularly restricted.

For example, it can be obtained by dissolving a reagent capable of converting a carbonyl compound to a derivative thereof in a suitable organic solvent, mixing the solution and a cation exchanger, then, removing the organic solvent, and if necessary, further washing the mixture with an organic solvent, then, removing the organic solvent. Examples of the organic solvent include aliphatic hydrocarbons such as hexane and the like, alicyclic hydrocarbons such as cyclohexane and the like, aromatic hydrocarbons such as benzene, toluene and the like, alcohols such as methanol, ethanol and the like, halogenated hydrocarbons such as chloroform, methylene chloride and the like. Removal of an organic solvent is usually conducted under a reduced pressure.

Further, a sampling material of the present invention can also be obtained by flowing a solution of a reagent capable of converting a carbonyl compound to a derivative thereof in the above-mentioned organic solvent through a column packed with a cation exchanger, then, removing the organic solvent, and if necessary, further washing with an organic solvent. Since a reagent capable of converting a carbonyl compound to a derivative thereof is often sold in the form of a hydrochloric acid salt, when it is to be supported on a weak acidic cation exchanger, the reagent capable of converting a carbonyl compound to a derivative thereof is previously neutralized with an alkali before being dissolved in an organic solvent for use. When it is to be supported on a strong acidic cation exchanger, a hydrochloride of the reagent capable of converting a carbonyl compound to a derivative thereof can be used as it is.

Further, an aqueous solution of a reagent capable of converting a carbonyl compound to a derivative thereof can also be used instead of an organic solvent solution of a reagent capable of converting a carbonyl compound to a derivative thereof. For example, the sampling material can be obtained by mixing an aqueous solution of a reagent capable of converting a carbonyl compound to a derivative thereof with a cation exchanger, then, removing water. Further, it can also be obtained by flowing an aqueous solution of a reagent capable of converting a carbonyl compound to a derivative thereof through a column packed with a cation exchanger, or immersing a column packed with a cation exchanger into an aqueous solution of a reagent capable of converting a carbonyl compound to a derivative thereof, then, removing water in the column. It is preferable to wash the cation exchanger previously with a phosphoric acid aqueous solution, phosphoric acid acetonitrile solution and the like, before contact of an aqueous solution of a reagent capable of converting a carbonyl compound to a derivative thereof with a cation exchanger. Even after contacting an aqueous solution of a reagent capable of converting a carbonyl compound to a derivative thereof with a cation exchanger to allow the reagent capable of converting a carbonyl compound to a derivative thereof to be supported on the cation exchanger, this cation exchanger is preferably washed with a phosphoric acid aqueous solution, phosphoric acid acetonitrile solution and the like.

In general, a reagent capable of converting a carbonyl compound to a derivative thereof is usually supported in an amount of 0.05 to 2 mg per 100 mg of the cation exchanger.

A sampling material for a carbonyl compound in a gas of the present invention is usually packed in a carbonyl compound sampling cartridge made of glass, plastic and the like, or used as a badge detector such as a film badge and the like.

A carbonyl compound sampling cartridge can be obtained by producing a sampling material for a carbonyl compound outside of a column, then, packing the column with the material. Further, it can also be obtained by flowing an organic solvent solution or aqueous solution of a reagent capable of converting a carbonyl compound to a derivative thereof through a column packed with a cation exchanger, or immersing a column packed with a cation exchanger into an aqueous solution and the like of a reagent capable of converting a carbonyl compound to a derivative thereof, as described above.

In use of the carbonyl compound sampling cartridge, a pump is usually connected to the carbonyl compound sampling cartridge to collect an air sample. For example, when the carbonyl compound sampling cartridge has an internal diameter of 0.3 to 15 cm, and a length of about 1 to 10 cm, the suction rate of the pump is preferably from about 0.03 to 1.5 L/min.

When an amine compound such as O-(2,3,4,5,6-pentafluorobenzyl)hydroxylamine and the like is used as the reagent capable of converting a carbonyl compound to a derivative thereof, a carbonyl compound in thus sucked sample is converted into an imine compound in the sampling cartridge. Therefore, the produced imine compound is eluted with an organic solvent, for example, an aliphatic hydrocarbon such as hexane and the like, an alicyclic hydrocarbon such as cyclohexane and the like, an aromatic hydrocarbon such as benzene, toluene and the like, alcohol such as methanol, ethanol and the like, a halogenated hydrocarbon such as chloroform, methylene chloride and the like, or a nitrile such as acetonitrile and the like. The quantitative analysis of the amount of carbonyl compounds in a gas can be effected by analyzing this eluted solution by liquid chromatography, gas chromatography and the like. Particularly, when the analysis is conducted by a capillary GC/MS method and the like, more accurate analysis is possible, meaning preferable phenomenon.

A carbonyl compound sampling cartridge of the present invention can be used also as a passive sampler. Further, a sampling material for a carbonyl compound of the present invention can be used also as a film badge. As a film badge for measuring carbonyl compounds such as formaldehyde and the like in working environment, that obtained by using a reagent capable of converting a carbonyl compound to a derivative thereof is known from JP-B No. 2-54906 and the like. The amount of carbonyl compounds in working environment can be measured effectively by making a sampling material for a carbonyl compound of the present invention, where a reagent capable of converting a carbonyl compound to a derivative thereof is supported on a cation exchanger, into a film, and attaching the film to the body of a worker.

EXAMPLES

The present invention will be specifically illustrated by the following examples.

First, examples for producing a sampling material for a carbonyl compound of the present invention will be shown.

Example 1

200 mg of a hydrochloride of O-(2,3,4,5,6-pentafluorobenzyl)hydroxylamine is dissolved in 100 ml of a 10% aqueous sodium hydroxide solution, and extracted with 200 ml of hexane to obtain a hexane solution of free O-(2,3,4,5,6-pentafluorobenzyl)hydroxylamine. To this is added 200 mg of Bondecyl SCX [chemical bonding type silica gel manufactured by Varian; benzenesulfonic acid type cation exchanger] and the mixture is stirred. Then, hexane is distilled off under a reduced pressure to obtain a sampling material for a carbonyl compound of the present invention.

Further, 0.5 g of the resultant sampling material for a carbonyl compound is packed in a glass column having an internal diameter of 8 mm and a length of 75 mm to provide a carbonyl compound sampling cartridge.

Example 2

200 mg of a hydrochloride of O-(2,3,4,5,6-pentafluorobenzyl)hydroxylamine is dissolved in 100 ml of a 105 aqueous sodium hydroxide solution, and extracted with 200 ml of hexane to obtain a hexane solution of free O-(2,3,4,5,6-pentafluorobenzyl)hydroxylamine. A glass column having an internal diameter of 8 mm and a length of 75 mm is packed with 500 mg of Bondecyl SCX [chemical bonding type silica gel manufactured by Varian; benzenesulfonic acid type cation exchanger] and 5 ml of the above-mentioned hexane solution is passed through this column. Then, the packed material is washed by flowing 5 ml of hexane tough it, and dried under a reduced pressure by an aspirator to obtain a carbonyl compound sampling cartridge packed with a sampling material for a carbonyl compound of the present invention.

Example 3

Bondelute JP [solid phase extraction column manufactured by Varian, packed with 500 mg of benzensulfonic acid ion exchanger (SCX)] (hereinafter, referred to as SCX) is washed with 3 mL of a 0.05% (v/v) phosphoric acid (guaranteed reagent) acetonitrile solution. Further, SCX is washed with 3 mL of a 0.05% phosphoric acid aqueous solution. Then, to SCX is added 3 mL of an O-(2,3,4,5,6-pentafluorobenzyl)hydroxylamine aqueous solution (3.3. mg/1 mL water). Then, SCX is washed with 3 mL of a 0.05% phosphoric acid aqueous solution. Thereafter, SCX is further washed with 3 mL of a 0.05% phosphoric acid acetonitrile solution. Thus obtained column is placed into a 1 L round bottomed flask and dried under a reduced pressure at room temperature. Then, the flask is sealed with a lure plug, and a carbonyl compound sampling cartridge (column) can be obtained.

Example 4

A column packed with a cation exchanger is immersed for a constant time in a bath filled with a 0.05% phosphoric acid acetonitrile solution. Then, it is lifted from the bath, and the 0.05% phosphoric acid acetonitrile solution is removed. Then, the column is immersed for a constant time in a bath filled with a 0.05% phosphoric acid aqueous solution, then, lifted from the bath, and the 0.05% phosphoric aqueous solution is removed. Further, thus obtained column is immersed for a constant time in a bath filled with an aqueous solution of a O-(2,3,4,5,6-pentafluorobenzyl)hydroxylamine hydrochloride (constant concentration; for example, 3.3 mg/1 mL water), then, lifted from the bath, and the aqueous solution of a O-(2,3,4,5,6-pentafluorobenzyl)hydroxylamine hydrochloride is removed. Thereafter, it is immersed for a constant time in a bath filled with a 0.05% phosphoric acid aqueous solution, then, lifted from the bath, and the 0.05% phosphoric acid aqueous solution is removed. Further, it is immersed for a constant time in a bath filled with a 0.05% phosphoric acid acetonitrile solution, then, lifted from the bath, and the 0.05% phosphoric acid acetonitrile solution is removed. Thereafter, it is dried under a reduced pressure at room temperature, and the column packed with this cation exchanger was sealed under atmosphere with no pollution, to obtain a carbonyl compound sampling cartridge (column).

Next, a method for measuring the concentration of formaldehyde in air using a carbonyl compound sampling cartridge packed with a sampling material for a carbonyl compound of the present invention will be illustrated by using a reference example.

Reference Example 1

10 L of a standard gas ($122 \times 10^3$ $\mu/m^3$, absolute amount: $0.122\mu$) of formaldehyde generated according to a method described in Eisei Kagaku vol. 42, 501 (1996) is sampled by sucking with a pump (flow rate: 0.2 L/min.) using a carbonyl compound sampling cartridge obtained in Example 2. Then, 20 ml of benzene is flowed through this carbonyl compound sampling cartridge to obtain an eluted benzene solution. The eluted benzene solution is analyzed by gas chromatography using a specimen of O-(2,3,4,5,6-pentafluorobenzyl)hydroxylamine formaldoxime. The result reveals that 95.3% of formaldehyde in the standard gas can be recovered according to the above-described procedure, and it is proved that the amount of formaldehyde in a gas can be detected with high accuracy by a carbonyl compound sampling cartridge of the present invention.

Reference Example 2

A carbonyl compound sampling cartridge obtained in Example 3 is left for 5 months at room temperature (20 to 25° C.), then, the same experiment as in Reference Example 1 is conducted. The recover ratio of formaldehyde is the same as in Reference Example 1, and no background of formaldehyde and acetaldehyde is found at all. Thus, excellent storage stability of a carbonyl compound sampling cartridge of the present invention can be proved.

Comparative Example 1

A sampling material for a carbonyl compound is obtained in the same manner as in Example 1 except that 200 mg of acidic silica gel is used instead of 200 mg of Bodecyl SCX.

Further, 0.5 g of the resultant sampling material for a carbonyl compound is packed in a glass column having an internal diameter of 8 mm and a length of 75 mm to obtain a carbonyl compound sampling cartridge.

Comparative Example 2

A sampling material for a carbonyl compound is obtained in the same manner as in Example 1 except that 200 mg of a 2,4-dinitrophenylhydrazine hydrochloride is used instead of 200 mg of an O-(2,3,4,5,6-pentafluorobenzyl)hydroxylamine hydrochloride, and 200 mg of acidic silica gel is used instead of 200 mg of Bodecyl SCX.

Further, 0.5 g of the resultant sampling material for a carbonyl compound is packed in a glass column having an internal diameter of 8 mm and a length of 75 mm to obtain a carbonyl compound sampling cartridge.

Reference Example 3

An eluted solution obtained by flowing 20 ml of cyclohexane through the carbonyl compound sampling cartridge obtained in Example 1, Comparative Example 1 or Comparative Example 2 is analyzed by gas chromatography. When a carbonyl compound sampling cartridge obtained in Example 1 of the present invention was used, formaldehyde and acetaldehyde were not detected at all. On the other hand, when carbonyl compound sampling cartridge obtained in Comparative Example 1 and Comparative Example 2 were used, formaldehyde and acetaldehyde were detected. Namely, it is proved that when a carbonyl compound sampling cartridge of the present invention is used, blank is extremely clear, and accurate measurement is possible even at lower concentration.

Reference Example 4

An eluted solution is obtained in the same manner as in Reference Example 1 using a carbonyl compound sampling cartridge obtained in Example 1 and Comparative Example 1, and the amount of O-(2,3,4,5,6-pentafluorobenzyl)hydroxylamine in the eluted solution is analyzed by gas chromatography. When a carbonyl compound sampling cartridge obtained in Example 1 of the present invention is used, the amount of O-(2,3,4,5,6-pentafluorobenzyl)hydroxylamine in the eluted solution is small. On the other hand, when a carbonyl compound sampling cartridge obtained in Comparative Example 1 is used, the amount of O-(2,3,4,5,6-pentafluorobenzyl)hydroxylamine in the eluted solution is large. Namely, it is proved that when a carbonyl compound sampling cartridge of the present invention is used, elution of a reagent capable of converting a carbonyl compound to a derivative thereof, O-(2,3,4,5,6-pentafluorobenzyl)hydroxylamine, is small, and, consequently, removal thereof is not necessary in quantitative analysis, and a carbonyl compound can be analyzed more simple than the conventional method.

Industrial Applicability

A sampling material for a carbonyl compound of the present invention enables analysis of carbonyl compounds such as formaldehyde and the like in a gas by a simpler manner at a high sensitivity and at high accuracy. Namely, elution of a reagent capable of converting a carbonyl compound to a derivative thereof is small, and a carbonyl compound can be detected even at low concentration at high accuracy. Further, the sampling material for carbonyl compound in a gas of the present invention has excellent storage stability. This material enables microanalysis of carbonyl compounds such as formaldehyde and the like in an indoor and outdoor air, and can be used for detecting aldehydes and the like not only in working environment but also in houses.

What is claimed is:

1. A sampling material for a carbonyl compound in a gas comprising O-(2,3,4,5,6-pentafluorobenzyl)hydroxylamine supported on a cation exchanger.

2. The sampling material for a carbonyl compound in a gas according to claim 1 wherein the cation exchanger is a sulfonic acid type cation exchanging resin, cellulose into which a sulfoethyl group has been introduced or silica gel into which a benzenesulfonic group has been introduced.

3. A sampling cartridge for a carbonyl compound in a gas wherein a sampling material for a carbonyl compound in a gas comprising O-(2,3,4,5,6-pentafluorobenzyl)hydroxylamine supported on a cation exchanger is packed in a column.

4. The sampling cartridge for a carbonyl compound in a gas according to claim 3 wherein the cation exchanger is a sulfonic acid type cation exchanging resin, cellulose into which a sulfoethyl group has been introduced or silica gel into which a benzenesulfonic group has been introduced.

5. A film badge obtained by combining a sampling material for a carbonyl compound comprising O-(2,3,4,5,6-pentafluorobenzyl)hydroxylamine supported on a cation exchanger with a film.

* * * * *